United States Patent

Buendia et al.

[11] 4,091,226
[45] May 23, 1978

[54] NOVEL CYCLOPENTENECARBOXYLATES

[75] Inventors: Jean Buendia, Nogent-sur-Marne; Michel Vivat, Lagny-sur-Marne, both of France

[73] Assignee: Roussel Uclaf, Paris, France

[21] Appl. No.: 746,824

[22] Filed: Dec. 2, 1976

[30] Foreign Application Priority Data

Dec. 18, 1975 France .................................. 75 38838

[51] Int. Cl.² ............................................ C07C 69/74
[52] U.S. Cl. .............................. 560/122; 260/348.48; 260/348.58; 542/400; 542/426; 560/121
[58] Field of Search ........ 260/468 D, 468 K, 514 DK

[56] References Cited

U.S. PATENT DOCUMENTS 3,736,319  5/1973  Martel et al. ..................... 260/240

Primary Examiner—Robert Gerstl
Attorney, Agent, or Firm—Hammond & Littell

[57] ABSTRACT

Novel cyclopentenecarboxylates of the formula

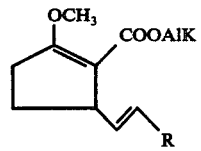

wherein Alk is alkyl of 1 to 4 carbon atoms and R is selected from the group consisting of —CHO and —CH₂OH and a process for their preparation and a process for the preparation of compounds of the formula

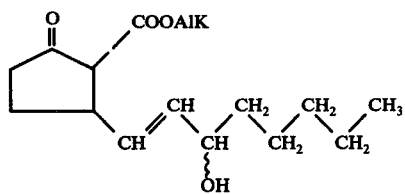

3 Claims, No Drawings

NOVEL CYCLOPENTENECARBOXYLATES

OBJECTS OF THE INVENTION

It is an object of the invention to provide the novel cyclopentenecarboxylates of formula I and a novel process for their preparation.

It is a further object of the invention to provide novel intermediates for the compounds of formula I.

It is another object of the invention to provide a novel process for the synthesis of the prostaglandins of formula B.

These and other objects and advantages of the invention will become obvious from the following detailed description.

THE INVENTION

The novel cyclopentenecarboxylates of the invention have the formula

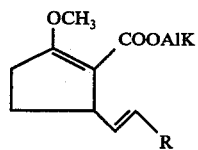

wherein AlK is alkyl of 1 to 4 carbon atoms and R is selected from the group consisting of —CHO and —CH$_2$OH.

Examples of suitable alkyl groups of 1 to 4 carbon atoms are methyl, ethyl, propyl, isopropyl, butyl, sec-butyl and tert.-butyl. Specific compounds of formula I are ethyl (5RS) (1'E) 2-methoxy-5-(2'-formylvinyl)-1-cyclopentenecarboxylate and ethyl (5RS) (1'E) 2-methoxy-5-(3'-hydroxy-1'-propenyl)-1-cyclopentenecarboxylate.

The process of the invention for the preparation of the compounds of formula I comprises reacting 4,5-epoxy-2-pentenal of the formula

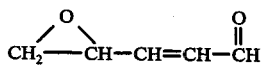

with a reducing agent to form 4,5-epoxy-2-penten-1-ol of the formula

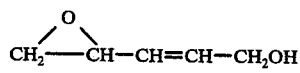

reacting the latter with a halogenating agent to form a compound of the formula

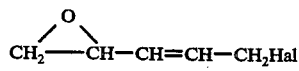

wherein Hal is chlorine or bromine, reacting the latter in the presence of a strong base with a compound of the formula

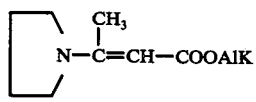

wherein AlK has the above definition to obtain a compound of the formula

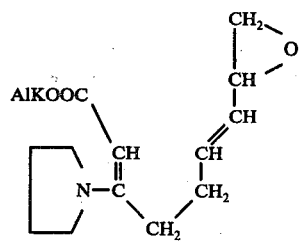

reacting the latter with first a base, then an acid and finally with diazomethane to obtain a compound of the formula

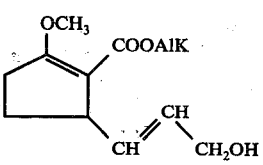

which can be treated with an oxidizing agent to form a compound of the formula

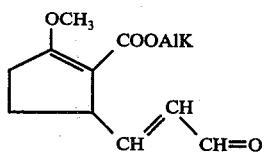

In a preferred embodiment of the invention, 4,5-epoxy-2-pentenal is reduced with sodium borohydride but other reducing agents such as sodium tris tert.-butoxyborohydride, lithium or potassium tris sec.-butoxyborohydride or lithium tris methoxy borohydride may also be used. The halogenating agent for reaction with 4,5-epoxy-2-penten-1-ol is preferably a bromination agent such as a complex of carbon tetrabromidetriphenyl phosphine but also useful are phosphorus tribromide in pyridine, a complex of carbon tetrachloride-triphenyl phosphine or phosphorus trichloride in pyridine.

The reaction of a compound of formula III with a strong base is preferably effected with butyl lithium but also useful are other strong bases such as methyl lithium, lithium diisopropyl amide or sodium or potassium amide. The treatment of the compound of formula V with a base and then an acid is preferably effected with lithium diisopropyl amide and an acid support such as silica but also useful are bases such as butyl lithium, methyllithium or sodium or potassium amide and other acids such as mineral acids like hydrochloric acid. The oxidizing agent used to treat a compound of formula I' is preferably silver silicate but other oxidizing agents such as silver carbonate, dichlorodicyanoquinone, manganese dioxide or chromic oxide in pyridine may be used.

The compounds of formula V may also be prepared by reacting a compound of formula III with an alkyl acetylacetate of the formula

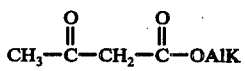

wherein AlK is alkyl of 1 to 4 carbon atoms in the presence of a strong base to obtain a compound of the formula

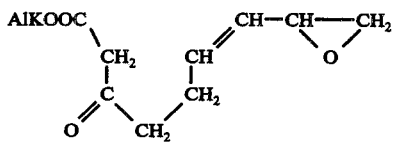

IV which is then treated with pyrollidine in the presence of an acid to obtain the corresponding compound of formula V.

In a preferred mode of the said process, the use of the strong base is preceeded by treatment with a weak base and preferably butyllithium is used but is preceeded by sodium hydride. The sodium hydride may be replaced by calcium carbonate, sodium or potassium carbonate or bicarbonate or an alkali metal alcoholate such as sodium or potassium methylate. The buthyllithium may be replaced by lithium diisopropyl amide, lithium diethyl amide or potassium in liquid ammonia. The butyllithium or one of these strong bases may also be used alone. The acid for treatment of the resulting product is preferably p-toluene sulfonic acid but other acids such as anhydrous hydrochloric acid may be used.

Another facet of the process of the invention for the preparation of compounds of formula I comprises treating a compound of formula V with first a base, then an acid and finally with diazomethane to obtain a compound of the formula

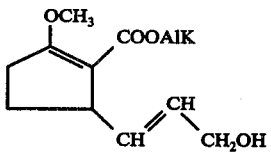

I' which may be oxidized with an oxidation agent to obtain a compound of the formula

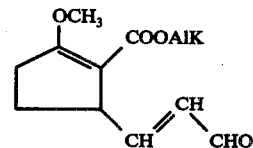

I"

Also part of the invention is the preparation of compounds of formula V by reacting a compound of formula III with a compound of the formula

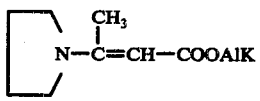

wherein AlK is alkyl of 1 to 4 carbon atoms in the presence of a strong base.

Also part of the invention is the preparation of a compound of formula III by reacting 4,5-epoxy-2-pentenal with a reducing agent to form 4,5-epoxy-2penten-1-ol which is then reacted with a halogenating agent to obtain a compound of formula III.

Among the novel intermediates of the invention are compounds of the formula

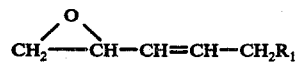

wherein $R_1$ is selected from the group consisting of —OH, —Br and —Cl and compounds of the formula

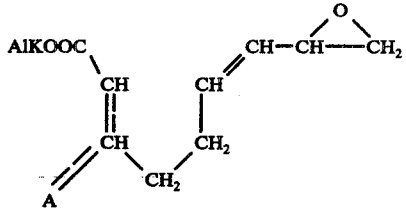

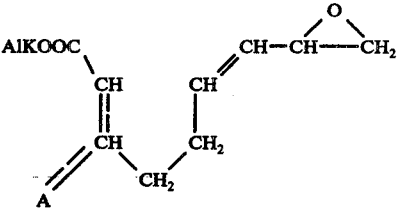

wherein AlK is alkyl of 1 to 4 carbon atoms and A is selected from the group consisting of

and $=O$ with the dotted lines indicating that there is a double bond towards A when A is $=O$ and the other dotted line forms a double bond when A is

The compounds of formula I have a great industrial interest since they permit novel synthesis for prostaglandin compounds which synthesis have advantages over the processes for the production of the said products. In contrast to the prior art processes, the synthesis using the intermediates of formula I are much easier to run and necessitates less purifications of the intermediates products and the synethesis is much shorter. The products of formula I are particularly useful for preparing prostaglandins with a 10,11-dihydro-PGA$_2$ structure.

The novel process of the invention for the preparation of prostaglandins of the formula

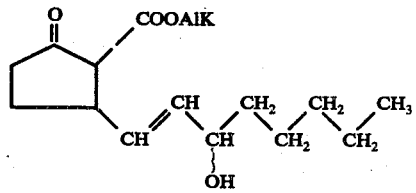

(B)

wherein AlK is alkyl of 1 to 4 carbon atoms and the wavy line indicates that the group may be in either of the two possible positions with respect to the carbon atom comprises reacting a compound of formula I" with an n-pentyl magnesium halide to form a compound of the formula

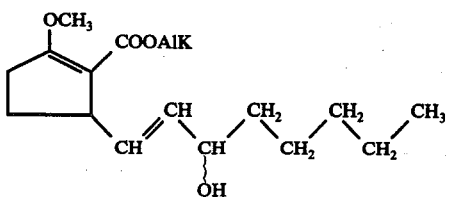

and treating the latter with an acid to form the corresponding compound of formula B.

In the preferred mode of the said process, the n-pentyl magnesium halide is the bromide but the chloride and the iodide may also be used. The reaction is effected under anhydrous conditions in an aprotic solvent such as ether or tetrahydrofuran. The acid used to form the compound of formula B is preferably hydrochloric acid but other acids such as oxalic acid or p-toluene sulfonic acid may also be used.

The compounds of formula B may be treated as described in French Pat. No. 2,085,652 to form a compound of the formula

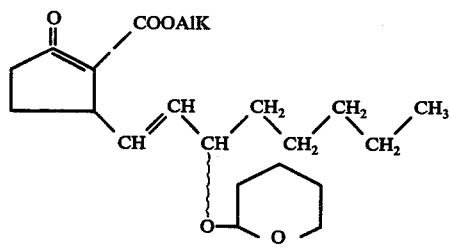

which can be reacted as described in French Pat. No. 2,085,654 to form prostanoic acid derivatives with a 10,11-dihydro $PGA_2$ structure which have interesting pharmacological properties. The compounds of formula I are also useful for the preparation of cyclopentanol derivatives having interesting pharmacological properties. A synthesis has been described previously which comprises reacting a compound of formula B with diazomethane and oxidizing the resulting product with an oxidizing agent such as silver silicate.

The products of formula I are thus useful for the preparation of a compound of the formula

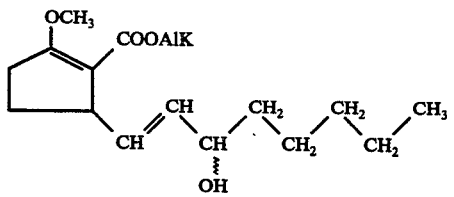

in a fewer number of steps than the prior art process by reacting a compound of formula I″ with a n-pentyl magnesium halide.

The preparation of cyclopentanol derivatives having interesting pharmacological properties starting with the compounds of formula VI is described in copending, commonly assigned U.S. patent application Ser. No. 717.048 filed Aug. 24, 1976, wherein a compound of formula VI is reacted with an oxidation agent to form a compound of the formula

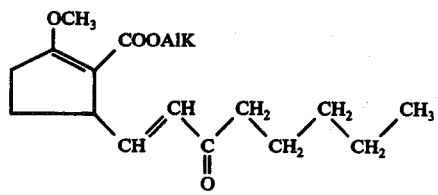

reacting the latter with a compound of the formula $$R^1-Mg-Hal$$

wherein Hal is halogen and $R^1$ is branched or straight chain, saturated or unsaturated aliphatic of 1 to 4 carbon atoms to obtain a compound of the formula

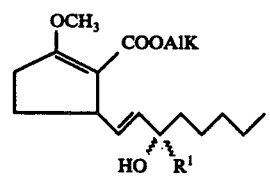

which is then treated with an acid such as hydrochloric acid to obtain a compound of the formula

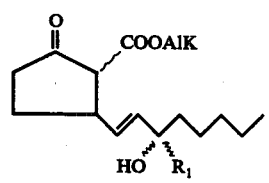

which may be either treated with a reducing agent such as sodium borohydride under mild conditions to form a compound of the formula

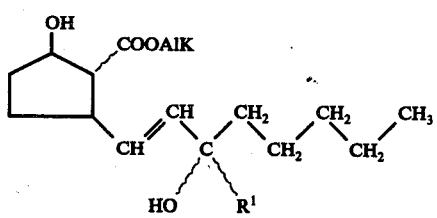

or reacted with 2,3-dihydropyran to obtain a compound of the formula

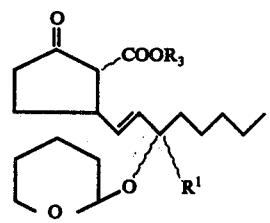

which may be treated with a reducing agent such as sodium borohydride under mild conditions to form a compound of the formula

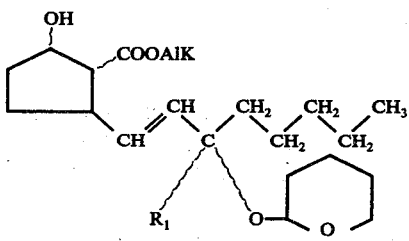

The compounds of formulae D and E are described in U.S. patent application Ser. No. 717,048 as having antagonistic properties against prostaglandins and having analgesic, anti-inflammatory and smooth muscle relaxant properties. They are useful for the treatment of pain affecting smooth muscles and articulations, pain, rhumatismal affections and affections due to a hyperactivity of certain smooth muscles.

The compounds of the formula

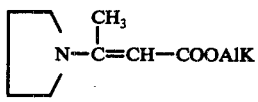

wherein AlK is alkyl of 1 to 4 carbon atoms may be prepared by reacting pyrrolidine in an acid media with an alkyl acetyl acetate.

In the following examples there are described several preferred embodiments to illustrate the invention. However, it is to be understood that the invention is not intended to be limited to the specific embodiments.

EXAMPLE 1

Ethyl (5RS) (1'E) 2-methoxy-5-(3'-hydroxy-1'-propenyl)-1-cyclopentenecarboxylate STEP A: (2E) 4,5-epoxy-2-pentene-1-ol 1.892 g of sodium borohydride were added in 3 portions to a mixture of 20 g of trans 4,5-epoxy-2-pentenal and 50 ml of ethanol under a nitrogen atmosphere at −30° C and the mixture was then stirred for an hour at −30° C. The mixture was added to an excess of acetone and was then stirred for 15 minutes. The mixture was poured into an iced monosodium phosphate solution and was then extracted with ethyl acetate. The extracts were dried and evaporated to dryness. The brown oil residue was chromatographed over silica gel and was eluted with a 50—50—2 cyclohexane-ethyl acetate-triethylamine mixture to obtain 12 g of (2E) 4,5-epoxy-2-pentene-1-ol.

STEP B: (2E) 1-bromo-4,5-epoxy-2-pentene 48 g of carbon tetrabromide were added to a mixture of 11 g of the product of Step A and 100 ml of methylene chloride cooled in an ice bath and after stirring the mixture for 5 minutes, 40 g of triphenyl phosphine were added thereto. The mixture was removed from the ice bath and was stirred for 15 minutes at room temperature. The solvent was evaporated under reduced pressure and the reaction mass was effloresced with ethyl ether and crystallization was effected with excess carbon tetrabromide, triphenyl phosphine and triphenyl phosphine oxide. The mixture was filtered and the solids were washed. The different organic phases were reassembled and the solvent was evaporated. The residue was chromatographed over silica gel and was eluted with a 20–80–2 ethyl ether-petroleum ether-triethylamine mixture to obtain 9.5 g of a very volatile oil which was (2E) 1-bromo-4,5-epoxy-2-pentene.

STEP C: Ethyl (6E) 8,9-epoxy-3-oxo-6-nonenoate

A solution of 1.742 g of ethyl acetylacetate in 5 ml of tetrahydrofuran was slowly added to a mixture of 672mg of sodium hydride in a 50% oil mixture in 10 ml of tetrahydrofuran cooled to 0° C and the mixture was held at 0° C for 30 minutes. 8.7 ml of 1.6N butyllithium in hexane was added dropwise at 0° C to the reaction mixture and after standing at 0° C for 30 minutes, the mixture was cooled to −60° C. A solution of 2.3 g of the product of Step B in 5 ml of anhydrous tetrahydrofuran was added to the mixture and the mixture was held at −60° C for 3 hours and then overnight at −20° C. The mixture was poured into an iced monosodium phosphate solution and was extracted with ethyl acetate. The extracts were washed, dried and evaporated to dryness to obtain a yellow oil residue. The latter was chromatographed over silica gel and was eluted with an 80–20–2 cyclohexane-ethyl acetate-triethylamine mixture to obtain 1.47 g of ethyl (6E) 8,9-epoxy-3-oxo-6-nonenoate in the form of an oil.

STEP D: Ethyl (6E) 8,9-epoxy-3-(N-pyrrolidino)-2,6-nonadienoate

A mixture of 2.5 g of the product of Step C, 20 ml of benzene, 4 ml of pyrrolidine and 3 crystals of p-toluene sulfonic acid was stirred for 24 hours and was evaporated to dryness under reduced pressure. The oily residue was taken up in toluene, chromatographed over alumina and was eluted with a 50–50–2 benzene-ethyl acetate-triethylamine mixture to obtain 1.56 g of ethyl (6E) 8,9-epoxy-3-(N-pyrrolidino)-2,6-nonadienoate.

STEP D': Ethyl (6E) 8,9-epoxy-3-(N-pyrrolidino)-2,6-nonadienoate

A mixture of 3.7 g of ethyl acetylacetate enamine and 100 ml of anhydrous tetrahydrofuran was cooled to −70° C and 11.2 ml of a solution of 1.87N butyllithium in cyclohexane were added thereto over 30 minutes. The mixture was then allowed to stand at −70° C for 30 minutes and at 0° C for an hour. The mixture was then cooled to −70° C again and 4.1 g of the product of Step B were added thereto. The mixture stood at −70° C for 2 hours and overnight at −20° C. The mixture was poured into an aqueous saturated sodium chloride solution and the mixture was extracted with ethyl acetate. The organic extracts were washed, dried and evaporated to dryness under reduced pressure to obtain 5.3 g of ethyl (6E) 8,9-epoxy-3-(N-pyrrolidino)-2,6-nonadienoate identical to the product of Step D.

STEP E: Ethyl (5RS) (1'E) 2-methoxy-5-(3'-hydroxy-1'-propenyl)-1-cyclopentenecarboxylate 4.5 g of diisopropylamine were added over 30 minutes under nitrogen to 30 ml of a solution of 1.5N methyl lithium in ether cooled to 0° C to obtain a solution of 1.25 M/1 of lithium diisopropylamide in ether. 20 ml of the said solution were added at −10° C under nitrogen to a mixture of 5.3 g of the product of Step D, 30 ml of ether and 5 ml of anhydrous tetrahydrofuran and the mixture was allowed to stand at 0° C for an hour. The mixture was poured in an aqueous saturated sodium chloride solution and the mixture was extracted with ethyl acetate. The organic extracts were washed and evaporated to dryness to obtain a brown oil. The latter was chromatographed over silica gel and elution with ethyl acetate yielded 2.4 g of a yellow oil. A mixture of 3.7 g of the said product and 50 ml of 1.5% diazomethane in methylene chloride stood for 15 hours at room temperature and the mixture was evaporated to dryness under reduced pressure. The residue was chromatographed over silica gel and was eluted with a 70-3-0-2 benzene-ethyl acetate-triethylamine mixture to obtain 1 g of ethyl (5RS) (1'E) 2-methoxy-5-(3'-hydroxy-1'-propenyl)-1-cyclopentenecarboxylate.

EXAMPLE 2

Ethyl (5RS) (1'E) 2-methoxy-5-(2'-formylvinyl)-1-cyclopentenecarboxylate

A mixture of 1.1 g of silver silicate and 50 ml of benzene was refluxed to completely eliminate any water and 300 mg of the product of Example 1 were added thereto. The mixture was refluxed for an hour and was filtered. The filtrate was washed with ethyl acetate and then was evaporated to dryness under reduced pressure to obtain 300 mg of ethyl (5RS) (1'E) 2-methoxy-5-(2'-formylvinyl)-1-cyclopentenecarboxylate as a raw oil.

I.R. Spectrum: 1692 $cm^{-1}$: carbonyl corresponding to aldehyde and conjugated ester; 1628 $cm^{-1}$: conjugated double bond of the cyclopentene ring; 2746 $cm^{-1}$: C-H of aldehyde; and 974 $cm^{-1}$: double bond conjugated with aldehyde carbonyl.

EXAMPLE 3

Ethyl (5RS, 3'SR and RS) (1'E) 2-methoxy-5-(3'-hydroxy-1'-octenyl)-1-cyclopentenecarboxylate A solution of 4 g of amyl bromide in 20 ml of tetrahydrofuran was added dropwise under nitrogen to a mixture of 800 mg of magnesium in 2ml of anhydrous tetrahydrofuran to obtain a solution containing 0.55 moles per liter of amyl magnesium bromide and 1.3 ml of the said solution was added dropwise at 0° C to a mixture of 100 mg of the product of Example 2 in anhydrous tetrahydrofuran and the reaction mixture stood at 0° C for an hour. The mixture was poured into a mixture of 1N hydrochloric acid, ice and ethyl acetate and the resulting mixture was extracted with ethyl acetate. The organic extracts were washed, dried and evaporated to dryness under reduced pressure to obtain 175 mg of ethyl (5RS, 3'RS and SR) (1'E) 2-methoxy-5-(3'-hydroxy-1'-octenyl)-1-cyclopentenecarboxylate in the form of a brown oil which was used as is for Example 4.

EXAMPLE 4

Ethyl (1RS, 5RS, 3'SR and RS) (1'E) 2-oxo-5-(3'-hydroxy-1'-octenyl)-cyclopentanecarboxylate A mixture of 177 mg of the product of Step C, 5 ml of ethanol, 3 ml of water and 1 ml of 1N hydrochloric acid was stirred at room temperature for 18 hours and was then evaporated to dryness. The residue was taken up in ethyl acetate and the organic phase was washed with water, dried and evaporated to dryness to obtain a yellow oil. The latter was chromatographed over silica gel and was eluted with a 70-30 benzene-ethyl acetate mixture to obtain 76 mg of ethyl (1RS, 5RS, 3'RS and SR) (1'E) 2-oxo-5-(3'-hydroxy-1'-octenyl)-cyclopentanecarboxylate containing the 2 isomers in the 3'-position. The Rf of 3'(SR) isomer was 0.23 (70-30 benzene-ethyl acetate eluant) and the Rf of the 3'(RS) isomer was 0.26.

I.R. Spectrum: 3594 $cm^{-1}$: hydroxy; 1752 and 1721 $cm^{-1}$: carbonyl; 970 $cm^{-1}$: double bond.

EXAMPLE 5

Ethyl (1RS, 2SR, 5RS, 3'SR) (1'E) 2-hydroxy-5-(3'-hydroxy-3'-ethynyl-1'-octenyl)-cyclopentanecarboxylate

STEP A: Ethyl (5RS) (1'E) 2-methoxy-5-(3'-oxo-1'-octenyl)-1-cyclopentenecarboxylate A mixture of 100 mg of the product of Example 3, 15 ml of benzene and 211 mg of 93% silver silicate was refluxed for an hour and the mixture was filtered. The filtrate was evaporated to dryness and the residue was chromatographed over silica gel and was eluted with an 8-2 benzene-ethyl acetate mixture containing 0.5% triethylamine to obtain 70 mg of ethyl (5RS) (1'E) 2-methoxy-5-(3'-oxo-1'-octenyl)-1-cyclopentenecarboxylate with an Rf = 0.2 in the said eluant.

STEP B: Ethyl (5RS, 3'RS) (1'E) 2-methoxy-5-(3'-hydroxy-3'-ethynyl-1'-octenyl)-1-cyclopentenecarboxylate and ethyl (5RS, 3'SR) (1'E) 2-methoxy-5-(3'-hydroxy-3'-ethynyl-1'-octenyl)-1-cyclopentenecarboxylate 3.3 ml of a solution of 0.9 M of ethynyl magnesium bromide [obtained from ethyl magnesium bromide and acetylene in tetrahydrofuran] were added at −10° C to a solution of 660 mg of the product of Step A in 10 ml of tetrahydrofuran and the mixture was stirred at −5° C until the starting material disappeared. The mixture was then poured into an aqueous saturated ammonium chloride solution and the mixture was extracted with ether. The ether extracts were dried and evaporated to dryness and the residue was chromatographed over silica gel and was eluted with a 9-1 methylene chloride-ethyl acetate mixture containing 0.5% triethylamine to recover 144 mg of the β-OH isomer with an Rf = 0.26 and 216 mg of the α-OH isomer with an Rf = 0.23 (with the above eluant).

STEP C: Ethyl (1RS, 5RS, 3'SR) (1'E) 2-oxo-5-(3'-hydroxy-3'-ethynyl-1'-octenyl)-cyclopentanecarboxylate A mixture of 1.135 g of the α-hydroxy isomer of Step B, 35 ml of ethanol, 3.5 ml of water and 0.87 ml of 1N hydrochloric acid was stirred at 20° C for 70 hours and was then extracted with ethyl acetate. The organic extracts were washed with water, dried and evaporated to dryness. The residue was chromatographed over silica gel and was eluted with an 8-2 benzene-ethyl acetate mixture to obtain 846 mg of ethyl (1RS, 5RS, 3'SR) (1'E) 2-oxo-5-(3'-hydroxy-3'-ethynyl-1'-octenyl)-cyclopentanecarboxylate with an Rf = 0.33 with the foregoing eluant mixture.

STEP D: Ethyl (1RS, 2SR, 5RS, 3'SR) (1'E) 2-hydroxy-5-(3'-hydroxy-3'-ethynyl-1'-octenyl)-cyclopentanecarboxylate 53 mg of sodium borohydride were added at 5° C to a mixture of 390 mg of the product of Step C, 10 ml of ethanol and 1 ml of water and the mixture was stirred for 2 hours. The mixture was poured into water and was then extracted with methylene chloride. The organic extracts were washed with water, dried and evaporated to dryness. The residue was chromatographed over silica gel and was eluted with an 8-2 benzene-ethyl acetate mixture to obtain 180 mg of ethyl (1RS, 2SR, 5RS, 3'SR) (1'E) 2-hydroxy-5-(3'-hydroxy-3'-ethynyl-1'-octenyl)-cyclopentanecarboxylate with an Rf = 0.13 with the foregoing eluant mixture.

Various modifications of the products and processes of the invention may be made without departing from the spirit or scope thereof and it should be understood that the invention is intended to be limited only as defined in the appended claims.

We claim:

1. A compound of the formula

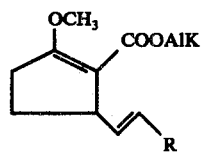

wherein Alk is alkyl of 1 to 4 carbon atoms and R is selected from the group consisting of —CHO and —CH$_2$OH.

2. A compound of claim 1 which is ethyl (5RS) (1'E) 2-methoxy-5-3'-hydroxy-1'-propenyl)-1-cyclopentenecarboxylate.

3. A compound of claim 1 which is ethyl (5RS) (1'E) 2-methoxy-5-2'-formylvinyl)-1-cyclopentenecarboxylate.